United States Patent [19]

D'Silva

[11] Patent Number: 4,514,392
[45] Date of Patent: Apr. 30, 1985

[54] PESTICIDAL ARYL N-(ALKYLTHIO-PHOSPHOROTHIO)ACYL-N-ALKYLCARBAMATES

[75] Inventor: Themistocles D. J. D'Silva, Chapel Hill, N.C.

[73] Assignee: Union Carbide Corporation, Danbury, Conn.

[21] Appl. No.: 509,707

[22] Filed: Jun. 30, 1983

[51] Int. Cl.³ .................... A01N 57/12; A01N 57/16; C07F 9/165
[52] U.S. Cl. .................... 514/148; 260/938; 514/97; 514/98; 514/99; 514/101; 549/7; 549/221
[58] Field of Search .............. 260/938; 424/211, 202, 424/203; 549/7, 221

[56] References Cited

U.S. PATENT DOCUMENTS

| | | | |
|---|---|---|---|
| 2,864,849 | 12/1958 | Schrader | 424/211 |
| 3,600,471 | 8/1971 | Haubein | 260/938 |
| 3,733,406 | 5/1973 | Haubein | 424/211 |
| 4,387,095 | 6/1983 | Saito et al. | 260/938 |

*Primary Examiner*—Anton H. Sutto
*Attorney, Agent, or Firm*—Clement J. Vicari

[57] ABSTRACT

Novel, aryl N-(alkylthio-phosphorothio)acyl carbamates represented by structure:

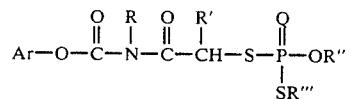

wherein the R groups represent various alkyl substituents, and Ar represents an aryl radical with various organic substituents, which exhibit superior insecticidal and miticidal activity.

18 Claims, No Drawings

PESTICIDAL ARYL N-(ALKYLTHIO-PHOSPHOROTHIO)ACYL-N-ALKYLCARBAMATES

FIELD OF THE INVENTION

The present invention relates to phosphorylated carbamate compounds useful as pesticides. More particularly, the present invention relates to aryl N-alkyl-N-(alkylthiophosphorothio)acylcarbamates useful as the active agents in pesticidal compositions for controlling insects and mites.

BACKGROUND OF THE INVENTION

U.S. Pat. No. 3,600,471 (Haubein I) and U.S. Pat. No. 3,733,406 (Haubein II) disclose phenyl N-dialkoxyphosphinothioacetyl-N-methylcarbamates wherein the dialkoxy radicals are methoxy or ethoxy and the phenyl radical is substituted with one or more substituents selected from the group of lower alkyl, alkenyl, alkoxy, alkenyloxy, or carboalkoxy radicals, chloro, cyano or nitro groups. These dialkoxyphosphinothioacetyl compounds possess only moderate insecticidal and miticidal activity.

SUMMARY OF THE INVENTION

The present invention is directed to aryl N-alkyl-N-(alkylthio-phosphorothio)acylcarbamate compunds which are useful as insecticides and miticides.

The claimed aryl N-(alkylthio-phosphorothio) acylcarbamates possess insecticidal and miticidal activity that is superior to the activity of the dialkoxy compounds of the prior art.

The invention is also directed to a process for the production of such compounds, insecticidal and miticidal compositions comprising an acceptable carrier and effective amount of such compounds, and methods for controlling insects and mites using such compounds.

DETAILED DESCRIPTION OF THE INVENTION

The aryl N-alkyl-N-(alkylthio-phosphorothio)acylcarbamates of this invention are represented by the structure:

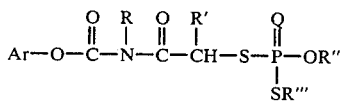

wherein:
Q is oxygen or sulfur;
R is $C_{1-4}$ alkyl;
R' is hydrogen or $C_{1-4}$ alkyl;
R'' is $C_{1-6}$ alkyl;
R''' is $C_3-C_6$ alkyl;
Ar is:

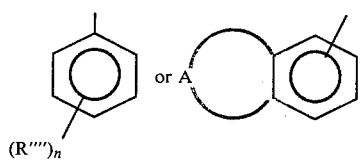

n is an integer having a value of zero to five; each R'''' is independently alkyl, halogen, alkoxy, alkylthio, alkenyloxy, alkynyloxy, dialkylamino, alkylthioalkyl, haloalkoxy, alkoxy-alkoxy, alkoxy-haloalkoxy, 2-(1,3-dithiolanyl), 2-(1,3-oxathiolanyl) or 2-(1,3-dioxalanyl) provided that no individual R'''' may contain more than six aliphatic carbon atoms; and A is a three or four membered, saturated or unsaturated, divalent chain composed of carbon atoms and not more than two oxygen or sulfur atoms wherein the carbon atoms of said chain may be substituted with one or more alkyl substituents containing no more than four carbon atoms each.

The bicyclic radicals represented by Ar include naphthyl, 5,6-dihydronaphthyl, 5,6,7,8-tetrahydronaphthyl, indenyl, indanyl, benzofuranyl, 2,3-dihydro-benzofuranyl, benzodioxanyl, benzothienyl, dihydrobenzothienyl, and benzodioxolanyl, all of which may be optionally substituted with $C_{1-4}$ alkyl groups.

Preferred aryl N-(alkylthio-phosphorothio)acyl-N-alkyl-carbamates include those in which R is methyl, R' is hydrogen, R'' is ethyl, R''' is n-propyl and Q is oxygen. Preferred bicyclic phenyl compounds are those in which Ar is a naphthyl, 5,6,7,8-tetrahydronaphthyl, or 2,3-dihydro-2,3-dimethylbenzofuraryl radical. Preferred monocyclic phenyl compounds are those in which the 2- or 4-phenyl positions are alkoxy, alkylthio or dialkylamino substituted and the 3- or 5-phenyl positions are unsubstituted or alkyl substituted.

The carbamates of the present invention can be prepared as outlined below:

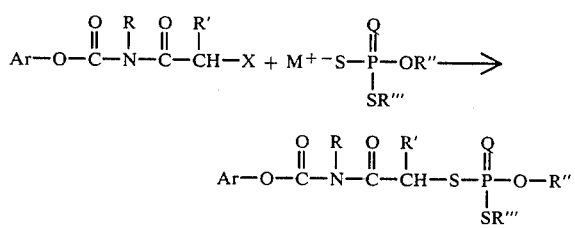

wherein Q, R, R', R'', R''' and Ar are as previously defined; X is a reactive halogen such as fluorine, chlorine or bromine; and M+ is an alkali metal or ammonium cation, which forms an ionic bond with phosphorothioate anions.

To prepare the aryl carbamates of this invention approximately stoichiometrically equivalent amounts of aryl α-haloacylcarbamate and alkylthio-phosphorothioate salt are reacted in a solvent which is inert under the reaction conditions utilized. Illustrative of such suitable solvents are aromatic hydrocarbons such as toluene, xylene, naphthalene, tetralin; aliphatic chlorinated hydrocarbons such as methylene chloride, chloroform, carbon tetrachloride, mono-, di- and tri-chloroethylene; low boiling aliphatic ketones and nitriles such as acetone, methylisobutyl ketone, methylethyl ketone, acetonitrile, propionitrile; and ethers such as diethylether, tertiary butyl methyl ether, dioxane and tetrahydrofuran.

The reaction is preferably conducted at ambient temperatures and pressures. However, temperatures of between about −20° to about 100° C., and pressures below or above atmospheric can be employed. The reaction is usually conducted under an inert atmosphere, such as nitrogen gas, with stirring, for a time sufficient to allow the reaction to proceed to completion. The inert gas will prevent any oxidation of the amine reactant and product that may occur in air.

The alkylthiophosphorothioate salts used above are known materials in the art and can be prepared in accordance with conventional methods known to those skilled in the art, such as the methods in U.S. Pat. No. 4,192,831 to Kiehs, et. al.

The aryl N-methyl-N-haloacylcarbamates used above can be prepared in two steps by the following preferred method:

METHOD I

Step 1:

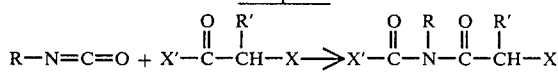

wherein X' is a reactive halogen and R, R' and X are as previously defined. Preferred reactive halogens are chlorine and fluorine. Approximately equimolar amounts of the desired alkyl isocyanate and haloacyl halide reactants both of which are available from commercial sources or which can be prepared by procedures known to those skilled in the art, are mixed together in the presence of a modified anhydrous zinc chloride catalyst. Reagent grade zinc chloride is premixed with silica gel and heated to above about 300° C. This modified zinc chloride catalyst should be maintained in an anhydrous atmosphere and used under anhydrous conditions.

Step 2:

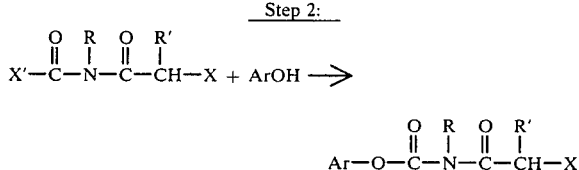

wherein X, X', Ar, R and R' are as previously defined. Approximately equimolar amounts of the chosen hydroxyaryl compound and the N-alkyl-N-haloacylcarbamoyl halide are mixed together, preferably in the presence of an acid acceptor such as sodium or potassium hydroxides or carbonates or alkylamines which will promote the reaction by accepting the by-product hydrohalic acid.

Alternatively, the aryl N-methyl-N-halocyl carbamates can be prepared as outlined below:

METHOD II

Step 1:

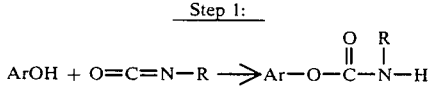

wherein Ar and R are as previously defined. Approximately equimolar amounts of hydroxyaryl compound and alkylisocyanate are mixed together, preferably in the presence of a catalyst such as a tertiary amine or a tin compound.

Step 2:

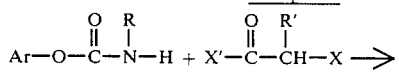

-continued
Step 2:

wherein Ar, R, R', X and X' are as previously defined. Approximately equimolar amounts of aryl N-methylcarbamate and haloacyl halide are mixed together and heated to about 60° C. for several hours.

Examples 1-6 are illustrative of the methods of preparing the intermediates and the novel compounds of this invention.

EXAMPLE 1

Preparation of 2,3-dihydro-2,2 dimethyl-7-benzofuranyl-N-chloracetyl-N-methylcarbamate A mixture of 1.0 g (0.006 m) of N-chloroacetyl-N-methylcarbamoyl chloride and 1.0 g (0.006 m) of 2,3-dihydro-2,2-dimethyl-7-benzofuranol in 15 cc dry toluene was stirred under nitrogen and 0.61 g (0.006 m) of triethylamine was added dropwise over a period of 10 mts. The mixture was stirred for an additional period of 2 hrs., filtered through a bed of celite and then the solvent was stripped off under reduced pressure to yield 1.39 g (yield 77%) of 2,3-dihydro-2,2-dimethyl-7-benzofuranyl N-chloroacetyl-N-methylcarbamate, a light yellow oil. NMR (CDCl$_3$): δ 7.3–6.6 (mn,3H); 4.75(s,2H); 3.40 (s,3H); 3.05 (s,2H) and 1.45 (s,6H). IR (CHCl$_3$): ν1760 and 1725 cm$^{-1}$

EXAMPLE 2

Preparation of 2,3-dihydro-2,2-dimethyl-7-benzofuranyl-N-chloroacetyl-N-methylcarbamate To a flask equipped with a reflux condenser, magnetic stirrer, thermometer and a drying tube were added 48.0 g (0.22 mol) of 7-(2,3-dihydro-2,2-dimethylbenzofuranyl)N-methylcarbamate and 88.0 g (0.79 mol) of chloroacetyl chloride. While stirring, the reaction mixture was heated at 60° C. for 48 hours. Excess chloroacetyl chloride was removed under reduced pressure. The dark yellow oil was dissolved in chloroform and the solution was filtered through a filter-bed of Fluorosil. The filtrate, after concentration, provided 59.0 g (yield: 93%) of a yellow viscous oil. NMR (CDCl$_3$): δ1.48 (S), 6H; 3.02 (S), 2H; 3.4 (S), 3H; 4.73 (S), 2H and 6.7–7.3 (br), 3H.

EXAMPLE 3

Preparation of 7-(2,3-dihydro-2,2-dimethylbenzofuranyl)N-(O-Ethyl-S-propyl-phosphorothioacetyl)-N-methylcarbamate To a solution of 12.0 g (0.04 mol) of 7-(2,3-dihydro-2,2-dimethyl-benzofuranyl)N-chloroacetyl-N-methylcarbamate (prepared in Example 1) dissolved in 100 ml of acetonitrile, 9.81 g (0.04 mol) dimethyl-ammonium O-ethyl-S-propyl-phosphorothioate were added dropwise. The reaction mixture was stirred under a nitrogen atmosphere for 64 hours and at 70° C. for 48 hours. On cooling the mixture was concentrated under reduced pressure. The viscous amber colored liquid was diluted with 300 ml of ethyl acetate and 100 ml of water. The organic layer was washed with water, dried over anhydrous magnesium sulfate, filtered and concentrated to yield 11.1 g of oil. The pure material was obtained by chromatography.

$C_{19}H_{18}NO_6PS_2$: Calcd: C, 49.45; H, 6.11; N, 3.03; Found: C, 49.62; H. 6.13; N, 3.00.

EXAMPLE 4

Preparation of 3,5-Dimethyl-4-methylthio-phenyl N-chloroacetyl-N-methylcarbamate A mixture of 11.27 g (0.05 mol) of 3,5-dimethyl-4-methylthiophenyl N-methyl-carbamate and 16.94 g (0.15 mol) of chloroacetyl chloride were heated under reflux for 6 hours and stirred at ambient temperature for 18 hours. An additional 11.29 g (0.1 mol) of chloroacetyl chloride were added and the reaction mixture was heated again under reflux for an additional period of 18 hours. The excess chloroacetyl chloride was removed under reduced pressure to afford 12.79 g (yield: 84.7%) of a yellow oil.

$C_{13}H_{16}ClNO_3S$: Calcd: C, 51.74; H, 5.34; N, 4.64; Found: C, 51.57; H, 5.34; N, 4.54.

EXAMPLE 5

Preparation of 3,5-dimethyl-4-methylthiophenyl N-(O-Ethyl-S-propyl-phosphorothioacetyl)-N-methyl carbamate To a solution of 10.4 g (0.034 mol) of 3,5-dimethyl-4-methylthio-phenyl N-chloroacetyl-N-methylcarbamate (prepared in Example 3) dissolved in 100 ml of acetonitrile, 9.5 g (0.038 mol) of dimethyl ammonium O-ethyl-S-propyl-phosphorothioate were added dropwise with stirring. The reaction mixture was heated at 70° C. for 18 hours. After concentration under reduced pressure, the residual oil was dissolved in ethyl acetate. The organic extract was washed successively with water, dilute sodium hydroxide and water. The organic layer was dried over anhydrous magnesium sulfate, filtered and concentrated under reduced pressure to yield 6.75 g of the product which was further purified by chromatography.

NMR (CDCl$_3$): δ0.9–2.0 (m) 6H; 2.15 (S) 3H; 2.52 (S) 6H; 2.4–3.2 (m) 2H; 3.34 (S) 3H; 3.8–4.5 (m) 4H; 6.88 (S) 2H.

EXAMPLE 6

Preparation of 3,4,5-trimethyl-phenyl N-(O-Ethyl-S-propyl-phosphorothioacetyl)-N-methylcarbamate The compound was prepared by the method used in Example 3 by reacting a solution of 12.0 g (0.044 mol) of 3,4,5-trimethyl-phenyl N-chloroacetyl-N-methylcarbamate in 100 ml of acetonitrile with 10.79 g (0.044 mol) of dimethyl-ammonium O-ethyl-S-propyl-phosphorothioate. The crude product was purified by high pressue liquid chromatography to yield 5.67 g of a clear oil.

$C_{18}N_{28}NO_5PS_2$: Calcd: C, 49.87; H, 6.51; N, 3.23; Found: C, 49.97; H, 6.60; N, 3.33.

The following compounds were also made by the above procedures:

: 1-naphthyl N-methyl-N-(O-ethyl-S-propyl-phosphorothioacetyl)carbamate;
Calcd. for $C_{19}H_{24}NO_5PS_2$:C,51.59;H,5.48;N,3.17 Found: C,52.86; H,5.71; N,3.36;

2-isopropoxyphenyl N-methyl-N-(O-ethyl-S-propyl-phosphorothioacetyl)carbamate;
Calcd: $C_{18}H_{28}NO_6PS_2$:C,48.08; H,6.28; N,3.16 Found: C,45.88; H,6.38; N,3.57;

2-(2-dioxalanyl)phenyl N-methyl-N-(O-ethyl-S-propyl-phosphorothioacetyl)carbamate;
Calcd. $C_{18}H_{26}NO_7PS_2$: C,46.66; H,5.65; N,3.02 Found: C, 45.70; H, 7.96; N, 3.43.

and 3,5-dimethyl-4-N,N-dimethylamino-phenyl N-methyl-N-(O-ethyl-S-propyl-phosphorothioacetyl)carbamate;
Calc for $C_{19}N_2O_5PS_2$:C,51.55;H,7.06N,6.30 Found: C,50.21; H,7.03; N,6.02.

Illustrative of my invention are the following compounds:

1-(5,6,7,8-tetrahydronaphthyl) N-(O-ethyl-S-propyl-phosphorothioacetyl)-N-methylcarbamate;
4-(2,2-dimethylbenzodioxalanyl) N-(O-ethyl-S-propyl-phosphorothioacetyl)-N-methylcarbamate;
4-(benzothienyl) N-(O-ethyl-S-propyl-phosphorothioacetyl)-N-methylcarbamate;
3-isopropylphenyl N-(O-ethyl-S-propyl-phosphorothioacetyl)-N-methylcarbamate;
3,5-dimethylphenyl N-(O-ethyl-S-propyl-phosphorothioacetyl)-N-methylcarbamate;
3,4-5-trimethylphenyl N-(O-ethyl-S-propyl-phosphorothioacetyl)-N-methylcarbamate;
3,5-dimethyl-4-dimethylaminophenyl N-(O-ethyl-S-propyl-phosphorothioacetyl)-N-methylcarbamate;
3,5-dimethyl-4-methylthiophenyl N-(O-ethyl-S-propyl-phosphorothioacetyl)-N-methyl-carbamate;
2-isopropoxyphenyl N-(O-ethyl-S-propyl-phosphorothioacetyl)-N-methylcarbamate;
2-chlorophenyl N-(O-ethyl-S-propyl-phosphorothioacetyl)-N-methylcarbamate;
2-methylphenyl N-(O-ethyl-S-propyl-phosphorothioacetyl)-N-methylcarbamate;
2-sec-butylphenyl N-(O-ethyl-S-propyl-phosphorothioacetyl)-N-methylcarbamate;
3-sec-butylphenyl N-(O-ethyl-S-propyl-phosphorothioacetyl)-N-methylcarbamate;
2-propargyloxyphenyl N-(O-ethyl-S-propyl-phosphorothioacetyl)-N-methylcarbamate;
2-ethylthiomethylphenyl N-(O-ethyl-S-propyl-phosphorothioacetyl)-N-methylcarbamate;
2-(1-methoxy-2-chloro)-ethoxyphenyl N-(O-ethyl-S-propyl-phosphorothioacetyl)-N-methylcarbamate;
2-(2-dioxalanyl)phenyl N-(O-ethyl-S-propyl-phosphorothioacetyl)-N-methylcarbamate;
2-(2-dithiolanyl)phenyl N-(O-ethyl-S-propyl-phosphorothioacetyl)-N-methylcarbamate;
3-methyl-4-dimethylaminophhenyl N-(O-ethyl-S-propyl-phosphorothioacetyl)-N-methylcarbamate;
1-naphthyl N-(O-ethyl-S-propyl-phosphorothioacetyl)-N-(n-propyl)carbamate; and
7-(2,3-dihydro-2,2-dimethylbenzofuranyl)N-(O-ethyl-S-propylphosphorothioacetyl)-N-(n-propyl)carbamate.

Aryl N-alkyl N-(alkylthio-phosphorothio)acyl-carbamates of the present invention were evaluated to determine their pesticidal activity against selected aphids, mites, worms, beetles and houseflies.

Solutions or suspensions of the test compounds 1–3 were prepared by dissolving 375 mg of compound in 7.5 ml of dimethylformamide. To this was added 15 ml of acetone in which had been dissolved 37.5 mg (10 percent of the weight of the compound) of an alkylphenol polyethoxyethanol surfactant as an emulsifying or dispersing agent. The resulting solution was mixed into 52.5 ml of water to give roughly 75 ml of a stock suspension or solution.

Solutions or suspensions of the test compounds 4–9 were prepared by dissolving one gram of compound in 50 ml of acetone in which had been dissolved 0.1 g (10 percent of the weight of the compound) of an alkylphenoxy polyethoxyethanol surfactant, as an emulsifying or dispersing agent. The resulting solution was mixed into 150 ml of water to give roughly 200 ml of a suspension containing the compound in finely divided form. The thus-prepared stock suspensions contained 0.5 percent by weight of compound. The concentrations in parts per million by weight employed in the tests described hereinbelow were obtained by appropriate dilutions of the stock suspension with water. The test procedures were as follows:

BEAN APHID FOLIAGE SPRAY TEST

Adults and nymphal stages of the bean aphid (*Aphis fabae* Scop.) reared on potted dwarf nasturtrium plants at 68°–70° F. and 50±5% relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids were placed on a revolving turntable and sprayed with 100–110 milliliters of test compound forumlation by use of a spray gun set at 40 psig air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during 24 hour holding period were 68°–70° F. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

MITE FOLIAGE SPRAY TEST

Adults and nymphal stage of the two-spotted mite (*Tetranychus urticae* Koch), reared on Tendergreen bean plants at 80±5% relative humidity, were the test organisms. Infested leaves from a stock culture were placed on the primary leaves of two bean plants 6 to 8 inches in height, growing in a 2½ inch clay pot. A sufficient number of mites for testing (150–200) were transferred from the excised leaves to the fresh plants in a period of 24 hours. Following the 24 hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5% relative humidity for 6 days, after which a mortality count of motile forms were made. Microscopic examination for motile forms were made on the leaves of the test plants. Any individual which was capable of location upon prodding was considered living.

SOUTHERN ARMYWORM LEAF SPRAY BAIT TEST

Larvae of the southern armyworm (*Spodoptera eridania*, (Cram.)), reared on Tendergreen bean plants at a temperature of 80°±5° F. and a relative humidity of 50±5%, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a spray gun set at 40 psig air pressure. This application, which lasted 25 seconds, was sufficient to wet plants to run-off. As a control, 100–110 milliliters of water-acetone-emulsifier solution containing no test compound were also sprayed on infested plants. When dry, the paired leaves were separated and each one was placed in a 9 centimeter petri dish lined with moistened filter paper. Five randomly selected larvae were introduced into each dish and the dishes were closed. The closed dishes were labeled and held at 80°–85° F. for three days. Although the larvae could easily consume the whole leaf within 24 hours, no more food was added. Larvae which were unable to move the length of the body, even upon stimulation by prodding, were considered dead. Percent mortality was recorded for various concentration levels. For compounds 1–3, the Seiva Pole lima bean plant was used instead of the Tendergreen bean plant both in the testing and rearing of the test insects.

MEXICAN BEAN BEETLE LEAF SPRAY TEST

Fourth instar larvae of the Mexican bean beetle (*Epilachna varivesti*, Muls.), reared on Tendergreen bean plants at a temperature of 80°±5° F. and 50±5% relative humidity, were the test insects.

The test compounds were formulatd by diluting the stock suspension with water to give a suspension containing 500 parts of test compound per million parts of final formulation. Tendergreen bean plants of standard height and age were placed on a revolving turntable and sprayed with 100–110 milliliters of test compound formulation by use of a spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter petri dish lined with moistened filter paper. Five randomly selected larvae were introduced into each dish, and the dishes were closed. The closed dishes were labeled and held at a temperature of 80°±5° F., for 3 days. Although the larvae could easily consume the leaf within 24 to 48 hours, no more food was added. Larvae which were unable to move the length of the body, even upon stimulation, were considered dead. For compounds 1-3, the Seiva Pole lima bean plant was substituted for the Tendergreen bean plant both in the testing and in the rearing of the test insects.

FLY BAIT TEST

Four to six day old adult house flies (*Musca domestica*, L.), reared according to the specifications of the Chemical Specialities, Manufacturing Association (Blue Book, McNair-Dorland Co., N.Y. 1954; pages 243-244, 261) under controlled conditions of 80°±5° F. and 50±5% relative humidity, were the test insects. The flies were immobilized by anesthetizing with carbon dioxide and 25 immobilized individuals, males and females, were transferred to a cage consisting of a standard food strainer about 5 inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the good strainer prior to admitting the anesthetized flies. The caged flies were allowed to feed on the bait for 24 hours, at a temperature of 80°±5° F. and a relative humidity of 50±5%. Flies which showed no sign of movement on prodding were considered dead.

The results of these tests are set forth in Table I below, using the following ratings:
A=excellent control at 500 ppm;
B=partial control at 500 ppm;
C=no control at 500 ppm.
It is to be understood that the compounds of this invention will exhibit greater control at levels of application above 500 ppm.

Suitable liquid diluents or carriers include water, petroleum distillates, or other liquid carriers with or without surface active agents. Liquid concentrates can be prepared by dissolving one of these compounds with a nonphytotoxic solvent such as acetone, xylene, or nitrobenzene, followed by dispersing the agents in water with the acids of a suitable surface active, emulsifying and dispersing agents.

The choice of dispersing and emulsifying agents and the amount employed depends on by the nature of the composition and the ability of the agent to facilitate the dispersion of the toxicant. Generally it is desirable to use as little of the agent as is possible, consistent with the desired dispersion of the toxicant in the spray so that rain does not re-emulsify the toxicant after it is applied to the plant and wash it off the plant. Non-ionic, anionic, amphoteric, or cationic dispersing and emulsifying agents can be employed, as for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, betonite, diatomaceous earth, fullers earth, and the like. In the formulation of the wettable powders the aforementioned dispersed agents as well as lignosulfonates can be included.

The required amount of the toxicants contemplated herein can be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

TABLE I
PESTICIDAL ACTIVITY OF ARYL N—PHOSPHOROTHIOACYL CARBAMATES

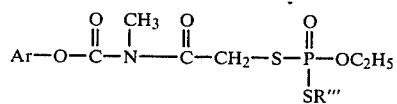

| Compound Number | Structure Ar | R''' | Bean Aphid | Mites | Southern Armyworm | Mexican Bean Beetle | Housefly |
|---|---|---|---|---|---|---|---|
| 1 | 3,5-dimethyl-4-methylthiophenyl | n-C3H7 | A | A | A | A | A |
| 2 | 2-isopropyloxyphenyl | n-C3H7 | A | A | A | A | A |
| 3 | 3,5-dimethyl-4-dimethylaminophenyl | n-C3H7 | A | A | A | A | A |
| 4 | 1-(5,6,7,8-tetrahydronaphthyl) | n-C3H7 | A | A | A | A | A |
| 5 | 1-naphthyl | n-C3H7 | B | A | A | A | A |
| 6 | 7-(2,2-dimethyl-2,3-dihydrobenzofuranyl) | n-C3H7 | A | A | A | A | A |
| 7 | 7-(2,2-dimethyl-2,3-dihydrobenzofuranyl) | —C2H5 | B | A | A | A | A |
| 8 | 3,4,5-trimethylphenyl | n-C3H7 | A | A | A | A | A |
| 9 | 2-(2-dioxalanyl) | n-C3H7 | A | A | A | A | A |

It can be seen from Table I that the representative carbamates of this invention exhibit pesticidal activity toward many insects and mites.

Compositions comprising an acceptable carrier and an pesticidally effective amount of such compounds can be prepared and applied in methods for controlling insects or mites according to well established procedures. Such compositions containing such compounds as the active agent will usually comprise a carrier and/or diluent, in either liquid or solid form.

The pesticides of this invention control the population of insects, mites and mite and insect ova upon plants or other material to which the pesticides are applied. Generally, when used in sufficient amout to kill or repel the insects, they do not burn or injure the plant. The toxicants are compatible with substantially any other constituents of the spray schedule, and they can be used in the soil, upon the seeds, or the roots of plants without injuring either the seeds or roots of plants.

They can also be used in combination with other pescicidally active compounds.

I claim:

1. Compounds having the structure:

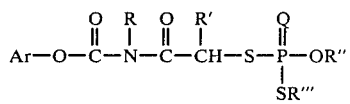

wherein:
Q is oxygen or sulfur;
R is $C_{1-4}$ alkyl;
R' is hydrogen or $C_{1-4}$ alkyl;
R'' is $C_{1-6}$ alkyl;
R''' is $C_3-C_6$ alkyl;
Ar is:

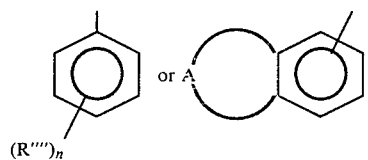

n is an integer having a value of zero to five;
each R'''' is independently alkyl, halogen, alkoxy, haloalkoxy, aloxy-alkoxy, alkoxy-haloalkoxy, alkylthio, alkenyloxy, alkynyloxy, dialkylamino, alkylthioalkyl, 2-(1,3-dithiolanyl), 2-(1,3-oxathiolanyl) or 2-(1,3-dioxalanyl) substituents in any combination provided that no individual R'''' may contain more than six aliphatic carbon atoms, and
A is a three or four membered, saturated or unsaturated, divalent chain composed of carbon atoms and not more than two oxygen or sulfur atoms wherein the carbon atoms of said chain may be substituted with one or more alkyl substituents containing no more than four carbon atoms each.

2. A method for controlling insects and mites comprised of subjecting them to a pesticidally effective amount of the compound of claim 1.

3. A compound in accordance with claim 1 wherein said R''' is n-propyl.

4. Compounds having the structure:

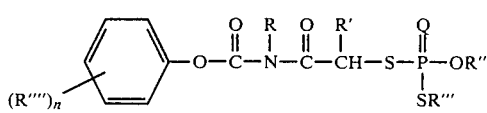

wherein:
Q is oxygen or sulfur;
R is $C_{1-4}$ alkyl;
R' is hydrogen or $C_{1-4}$ alkyl;
R'' is $C_{1-6}$ alkyl;
R''' is $C_3-C_3$ alkyl;
n is an integer from zero to five; and
each R'''' is independently hydrogen, alkyl, halogen, alkylthio, alkoxy, alkenyloxy, alkynyloxy, dialkylamino, alkylthioalkyl, alkoxyalkyl, haloalkoxy, alkoxy-alkoxy or alkoxy-haloalkoxy.

5. Compounds in accordance with claim 4 having the structure:

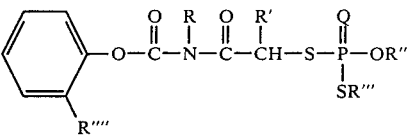

wherein said R'''' is $C_{1-4}$ alkoxy.

6. In accordance with claim 4, the compound 2-isopropoxyphenyl N-methyl-N-(O-ethyl-S-propyl-phosphorothio)acetylcarbamate.

7. Compounds in accordance with claim 4 having the structure:

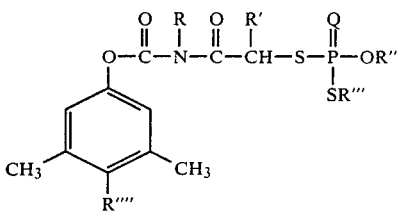

wherein said R'''' is $C_{1-4}$ alkyl, $C_{1-4}$ alkoxy, $C_{1-4}$ alkylthio, or di-$C_{1-4}$ alkyl-amino.

8. In accordance with claim 4, the compound 3,5-dimethyl-4-dimethylaminophenyl N-methyl-N-(O-ethyl-S-propyl-phosphorothio)acetylcarbamate.

9. In accordance with claim 4, the compound 3,5-dimethyl-4-methylthiophenyl N-methyl-N-(O-ethyl-S-propyl-phosphorothio)acetylcarbamate.

10. Compounds having the structure:

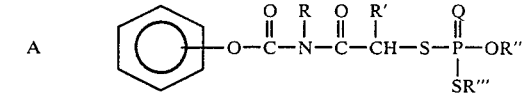

wherein:
Q is oxygen or sulfur;
R is $C_{1-4}$ alkyl;
R' is hydrogen or $C_{1-4}$ alkyl;
R'' is $C_{1-6}$ alkyl; and
R''' is $C_3-C_6$ alkyl;
A is three or four membered, saturated or unsaturated divalent chain composed of carbon atoms and not more than two oxygen or sulfur atoms, wherein the carbon atoms of said chain may be substituted with one or more alkyl substituents containing no more than four carbon atoms each.

11. In accordance with claim 10, the compound 1-naphthyl N-methyl-N-(O-ethyl-S-propyl-phosphorothio)acetylcarbamate.

12. In accordance with claim 10, the compound 1-(5,6,7,8-tetrahydronaphthyl) N-methyl-N-(O-ethyl-S-propyl-phosphorothio)acetylcarbamate.

13. In accordance with claim 10, the compound 7-(2,3-dihydro-2,2-dimethylbenzofuranyl)N-methyl-N-(O-ethyl-S-propyl-phosphorothio)acetylcarbamate.

14. A method in accordance with claim 2 wherein said compound is 3,5-dimethyl-4-dimethylaminophenyl N-methyl-N-(O-ethyl-S-propyl-phosphorothio)acetylcarbamate.

15. A method in accordance with claim 2 wherein said compound is 1-naphthyl N-methyl-N-(O-ethyl-S-propyl-phosphorothio)acetylcarbamate.

16. An insecticidal and miticidal composition comprising an acceptable carrier and a pesticidally effective amount of the compound of claim 1 as the active toxicant.

17. A composition in accordance with claim 16 wherein said active toxicant is the compound 3,5-dimethyl-4-dimethylaminophenyl N-methyl N-(O-ethyl-S-propyl-phosphorothio)acetylcarbamate.

18. A composition in accordance with claim 2 wherein said active toxicant is the compound 1-naphthyl N-methyl-N-(O-ethyl-S-propyl-phosphorothio)acetylcarbamate.

* * * * *

UNITED STATES PATENT AND TRADEMARK OFFICE
CERTIFICATE OF CORRECTION

PATENT NO. : 4,514,392

DATED : April 30, 1985

INVENTOR(S) : Themistocles D.J. D'Silva

It is certified that error appears in the above-identified patent and that said Letters Patent is hereby corrected as shown below:

In the claims, claim 4, that portion reading "R"' is $C_3$-$C_3$ alkyl" should read --R"' is $C_3$-$C_6$ alkyl--.

In the claims, claim 10, that portion reading

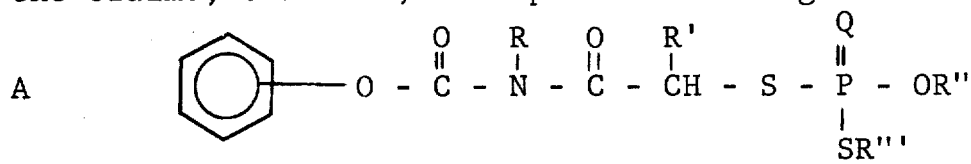

should read $$A\text{–}\bigcirc\text{–}O-\underset{\underset{O}{\|}}{C}-\underset{\underset{R}{|}}{N}-\underset{\underset{O}{\|}}{C}-\underset{\underset{R'}{|}}{CH}-S-\underset{\underset{SR'''}{|}}{\overset{\overset{Q}{\|}}{P}}-OR''$$

UNITED STATES PATENT AND TRADEMARK OFFICE
CERTIFICATE OF CORRECTION

PATENT NO. : 4,514,392
DATED : April 30, 1985
INVENTOR(S) : Themistocles D.J. D'Silva It is certified that error appears in the above-identified patent and that said Letters Patent is hereby corrected as shown below:

In the specification, column 6, line 9, that portion reading "$C_{19}N_2O_5PS_2$" should read --$C_{19}H_{31}N_2O_5PS_2$--.

Signed and Sealed this

Thirteenth Day of August 1985

[SEAL]

*Attest:*

DONALD J. QUIGG

*Attesting Officer*     *Acting Commissioner of Patents and Trademarks*